United States Patent [19]

Yamazaki et al.

[11] 4,201,877
[45] May 6, 1980

[54] PROCESS FOR PRODUCING A LINEAR TRIMER OF PARAISOPROPENYL PHENOL

[75] Inventors: Noboru Yamazaki; Teruo Yuasa, both of Nagoya; Yoshio Morimoto, Tokai; Kunio Aoi, Ichinomiya; Tsutomu Takase, Nagoya, all of Japan

[73] Assignee: Mitsui Toatsu Chemicals Inc., Tokyo, Japan

[21] Appl. No.: 961,451

[22] Filed: Nov. 16, 1978

[30] Foreign Application Priority Data

Nov. 26, 1977 [JP] Japan .................. 52/141126

[51] Int. Cl.² .............................................. C07C 37/00
[52] U.S. Cl. ................................................... 568/720
[58] Field of Search ........................................ 568/720

[56] References Cited

U.S. PATENT DOCUMENTS

| | | | |
|---|---|---|---|
| 2,972,599 | 2/1961 | Guest et al. | 568/720 |
| 3,137,677 | 6/1964 | Bolgiano | 568/720 |
| 3,288,864 | 11/1966 | Farnham | 568/720 |
| 4,054,611 | 10/1977 | Mimaki et al. | 568/756 |

Primary Examiner—Norman Morgenstern
Attorney, Agent, or Firm—Sherman & Shalloway

[57] ABSTRACT

A novel trimer of p-isopropenyl phenol of the structure

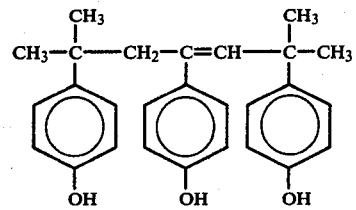

which is useful as a material or a curing agent for epoxy resins. The linear trimer includes a cis-isomer (m.p. 225.5°–227° C.) and a trans-isomer (m.p. 167°–168° C.). It is prepared by reacting p-isopropenyl phenol or its linear polymer in the presence of an acid catalyst such as sulfuric acid, boron fluoride or activated clay in an aromatic hydrocarbon, halogenated hydrocarbon, substituted aromatic hydrocarbon or aprotic polar solvent (e.g., benzene, carbon tetrachloride, nitrobenzene or dioxane).

10 Claims, 2 Drawing Figures

PROCESS FOR PRODUCING A LINEAR TRIMER OF PARAISOPROPENYL PHENOL

This invention relates to a process for producing linear trimer of p-isopropenyl phenol, and.

The present invention provides a process for producing a novel linear trimer of p-isopropenyl phenol represented by the formula

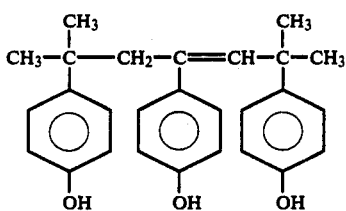

which is termed 2,6-dimethyl-2,4,6-tris(4-hydroxyphenyl)-hept-3-ene. This linear trimer includes cis- and transgeometric isomers.

Figure 1:
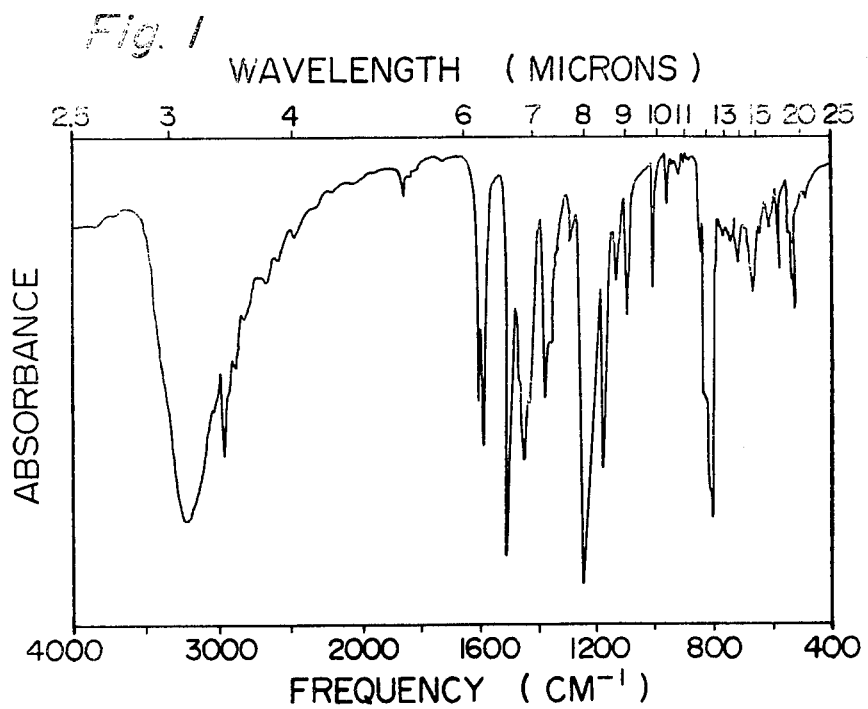
Figure 2:
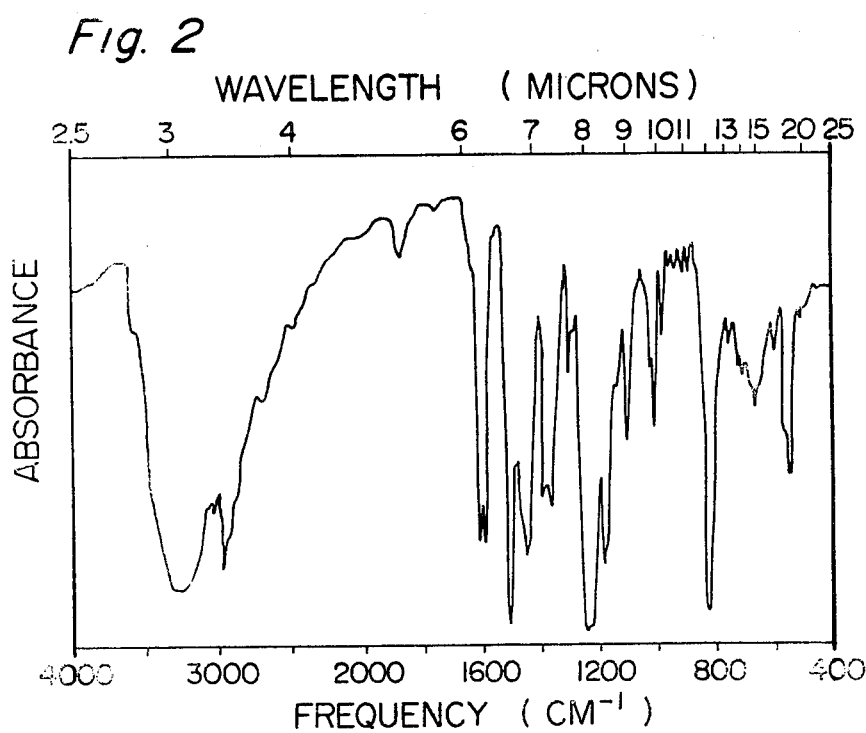

FIGS. 1 and 2 are infrared absorption spectra of the linear trimers obtained in Examples 1 and 10, respectively.

One known linear trimer of p-isopropenyl phenol is 4,6-dimethyl-2,4,6-tris(4-hydroxyphenyl)-hept-2-ene of the formula

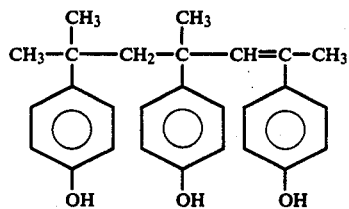

The compound of formula [II] is produced by adding 37% hydrochloric acid to a 50% acetic acid solution of monomeric p-isopropenyl phenol to adjust the pH of the solution to 1, and reacting the solution at 25° C. for 18 to 24 hours, as disclosed in U.S. Pat. No. 3,288,864. According to this method, the final desired product is difficult to isolate, and a long period of time is required for its production. Hence, it cannot permit low-cost commercial production.

U.S. Pat. No. 4,054,611 states that p-isopropenyl phenol is a readily polymerizable compound which polymerizes to a polymer expressed by the formula

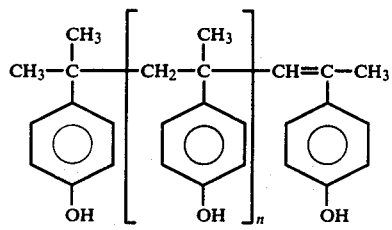

or

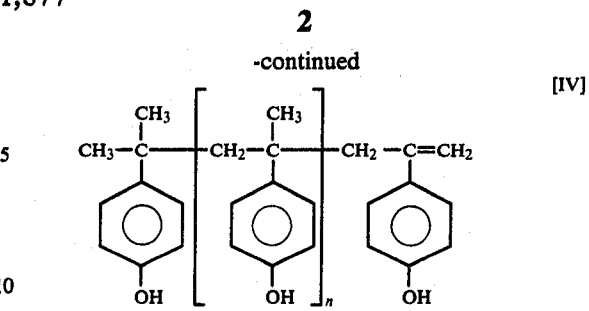

wherein n is 0 or an integer of 1 or more. A polymer of formula [III] in which n is 1 corresponds to the linear trimer of p-isopropenylphenol of formula [II]. A polymer of formula [IV] in which n is 1 has a somewhat different structure from the linear trimer of p-isopropenylphenol expressed by formula [II].

Although some linear trimers of p-isopropenyl phenol have been known as described above, a compound of formula [I] has not yet been known.

According to this invention, the linear trimer of p-isopropenyl phenol expressed by formula [I] can be advantageously produced by reacting at least one compound selected from the group consisting of p-isopropenyl phenol and linear polymers of p-isopropenyl phenol in the presence of an acid catalyst in an organic solvent.

The method for producing p-isopropenyl phenol, one of the starting materials in this invention, is well known. It can be obtained, for example, by heating bisphenol A to a high temperature in the presence of a basic catalyst to cleave it into phenol and p-isopropenyl phenol, distilling out these products under reduced pressure out of the reaction system, rapidly cooling the distillates to a temperature below the melting point of these distillates to solidify them, and recrystallizing the resulting solid from a solvent. p-Isopropenylphenol can be used as a starting material in this invention either singly or together with linear polymers of p-isopropenyl phenol.

The linear polymer of p-isopropenyl phenol, as another starting material in this invention, is a linear polymer of p-isopropenyl phenol of formula [III] or [IV] above, or mixture thereof having a degree of polymerization of 2 to 10 (n is 0 to 8 in formula [III] or [IV]). This linear polymer is obtained, for example, by heating bisphenol A in the presence of a basic catalyst to cleave it into phenol and p-isopropenyl phenol, distilling out these products out of the reaction system under reduced pressure, cooling the distillates to liquefy them, and then removing the phenol from the liquefied product by vacuum distillation. Since p-isopropenyl phenol is readily polymerizable, especially in the liquid state, and therefore, while p-isopropenyl phenol is maintained liquid (namely, from the liquefaction to the end of vacuum distillation), a part or a greater part of it polymerizes to a linear polymer. Sometimes, this linear polymer contains monomeric p-isopropenyl phenol, but can be used as a starting material in this invention without any degradative effect.

p-Isopropenyl phenol can also be obtained by dehydrogenating p-isopropyl phenol at 500° to 600° C. by using a chromia-alumina catalyst, or by decomposing p-2-hydroxy-2-propyl-α,α'-dimethylbenzylhydroperoxide obtained by oxidation of p-diisopropyl benzene, in the presence of an acid catalyst. Heating of such p-isopropenyl phenol in the liquid state can afford its linear polymers of formula [III] or [IV]. p-Isopropenylphenol and linear polymers thereof thus obtained can also be used as starting materials in this invention.

The linear polymers may have a structure of formula [III] or [IV], or a mixture thereof. When the linear polymer is used as a starting material in this invention, the linear trimer of p-isopropenyl phenol of formula [I] can be formed not only from a dimer but also from a trimer or higher polymer when the above linear polymers are used as starting materials in this invention.

Japanese Patent Publication No. 10869/77 discloses that a linear polymer of p-isopropenyl phenol containing a major proportion of a mixture of 4-methyl-2,4-bis(4-hydroxyphenyl)-pent-1-ene and 4-methyl-2,4-bis(4-hydroxyphenyl)-pent-2-ene, two isomeric dimers of p-isopropenyl phenol, is obtained by a process which comprises heating bisphenol A in the presence of a basic catalyst to cleave it, distilling off phenol from the resulting cleavage product containing the phenol, monomeric p-isopropenyl phenol and a linear polymer of p-isopropenyl phenol to form a mixture containing less than 10% by weight of phenol, and heating the mixture to 80° to 150° C. Usually, the above linear dimers of p-isopropenyl phenol include at least 85% by weight of 4-methyl-2,4-bis(4-hydroxyphenyl)-pent-1-ene and not more than 15% by weight of 4-methyl-2,4-bis(4-hydroxyphenyl)-pent-2-ene. The analysis made by the present inventors led to the confirmation that the linear polymer of p-isopropenyl phenol obtained by the above method contains at least 80% by weight of the above dimeric mixture, 7 to 13% by weight of a linear trimer of formula [III] or [IV], 5 to 9% by weight of a linear tetramer, and 2 to 4% by weight of a pentamer or higher polymer. This linear polymer of p-isopropenyl phenol containing the linear dimers as a major component can be used as a starting material in this invention either as such or after recrystallization to remove the other ingredients.

Since p-isopropenyl phenol is unstable and readily polymerizable, it is difficult to handle as a starting material. On the other hand, the rate of formation of the linear trimer of p-isopropenyl phenol of formula [I] from a linear polymer of p-isopropenyl phenol having a degree of polymerization of 4 or more is relatively slow. In contrast, the above linear dimers of p-isopropenyl phenol and linear polymer of p-isopropenyl phenol containing these dimers as a major ingredient are easy to handle and readily soluble in organic solvents, and the rate of formation of the linear trimer of p-isopropenyl phenol of formula [I] from these materials is sufficiently fast. Accordingly, they are especially suitable as starting materials for the linear trimer of p-isopropenyl phenol of formula [I].

In the production of the linear trimer of p-isopropenyl phenol of formula [I] in this invention, an organic solvent is used. Examples of useful organic solvents are aromatic hydrocarbons such as benzene, toluene or xylene; halogenated hydrocarbons such as methylene chloride, carbon tetrachloride, chloroform or ethylene dichloroide; substituted aromatic hydrocarbons such as nitrobenzene, anisole or chlorobenzene; and aprotic polar solvents such as dioxane, dimethyl formamide, dimethyl acetamide, acetonitrile, nitromethane or tetrahydrofuran. These organic solvents can be used either singly or as a mixture of two or more. A mixture of an aromatic hydrocarbon with water or an alcohol such as methanol or ethanol can also be used. In this case, the amount of water is preferably not more than 3.0% by weight based on the total weight of the mixture, and the amount of the alcohol is preferably not more than 70% by weight based on the total weight of the mixture. The amount of the organic solvent is not particularly critical. Usually, it is 20 to 1,000 parts by weight, preferably 50 to 200 parts by weight, per 100 parts by weight of the starting material.

Examples of the acid catalyst used in the production of the linear trimer of p-isopropenyl phenol of formula [I] include Lewis acids such as aluminum chloride, ferric chloride, stannic chloride or boron trifluoride, protonic acids such as sulfuric acid, phosphoric acid, hydrochloric acid, perchloric acid, benzenesulfonic acid, toluenesulfonic acid or methanesulfonic acid; and solid acids such as silica alumina, activated clay or cation exchange resins. The acid catalyst is used generally in an amount of 0.001 to 10 parts by weight per 100 parts by weight of the starting material. The especially preferred amount is 0.01 to 0.5 part for the protonic acid, cation exchange resin or Lewis acid, and 1 to 2 parts by weight for the activated clay, both per 100 parts by weight of the starting material.

The reaction temperature is generally from 0° C. to 100° C., preferably 35° to 65° C. At higher than 100° C., side-reactions such as the formation of a cyclic dimer of p-isopropenyl phenol tend to take place, and the yield of the desired product decreases. At lower than 0° C., oligomers of p-isopropenylphenol having a higher molecular weight than the trimer tend to form.

The reaction time is not particularly limited, but the suitable time is 0.1 to 10 hours.

The ratio between the cis- and trans-isomers of the linear trimer of p-isopropenyl phenol of formula [I] has closely to do with the reaction temperature and time. When the reaction is performed under the aforesaid conditions, the trans-isomer generally forms earlier, and the formation of the cis-isomer is delayed. For this reason, when the reaction time is relatively short, the product contains a higher proportion of the trans-isomer and a lower proportion of the cis-isomer. However, on continuing the reaction, isomerization of the trans-isomer to the cis-isomer takes place. Thus, when the reaction is performed for a relatively long time, the product contains a higher proportion of the cis-isomer and a lower proportion of the trans-isomer.

This tendency is more outstanding as the reaction temperature is higher. For example, when the reaction temperature is at least 65° C., the linear trimer formed by reaction within 1 hour consists of 80 to 90% of a trans-isomer and the remainder being a cis-isomer. When the reaction is performed for 4 hours or more, the product contains 80 to 90% of the cis-isomer, and the remainder being the trans-isomer. At a lower reaction temperature, the above tendency is less outstanding, and even when the reaction time is relatively short, the proportion of the cis-isomer in the product is higher. For example, when the reaction is performed at 60° C. for about 2 hours, the cis-isomer becomes a major ingredient of the product, and the proportion of the trans-isomer decreases. Accordingly, products having the cis-isomer and the trans-isomer in various desired ratios can be obtained by properly choosing the reaction temperature and time.

Specifically, the linear trimer of p-isopropenyl phenol of formula [I] is produced, for example, by feeding p-isopropenyl phenol and/or a linear polymer of p-isopropenyl phenol as a starting material and an organic solvent into a reactor, maintaining them at a predetermined temperature with stirring, adding a suitable amount of an acid catalyst, and maintaining the mixture for a certain predetermined period of time. The reaction can be performed in an atmosphere of air, and an inert gaseous atmosphere such as nitrogen or helium is not essential. Preferably, the starting material is kept uniformly dissolved in the organic solvent at the time of adding the acid catalyst and initiating the reaction. However, even when the material is not uniformly dissolved at this time, it will be so dissolved as the reaction proceeds after the addition of the acid catalyst.

When a non-polar organic solvent such as an aromatic hydrocarbon or halogenated hydrocarbon is used as the solvent in the above reaction, the product precipitates as crystals as the reaction proceeds. On the other hand, no precipitation of the product takes place when a polar organic solvent such as dimethyl formamide, dioxane, nitrobenzene or acetonitrile is used.

The composition of the reaction mixture is intermittently analyzed by gas chromatography, and when no change is noted in the concentrations of the starting materials, the reaction is regarded as terminated.

After the reaction, an aqueous solution of an alkali such as sodium hydroxide, potassium hydroxide, sodium carbonate or potassium carbonate is added to neutralize the acid catalyst.

After the neutralization of the acid catalyst, the reaction product is separated from the reaction mixture by various methods depending upon the state of the reaction mixture. Specifically, when the organic solvent is non-polar and therefore, the product separates as a precipitate, the final product is obtained by filtration. When the organic solvent is polar and therefore, the product is not precipitated, a non-polar solvent such as benzene is added to the reaction mixture to dilute it and thereby to precipitate the product as crystals. The final product is obtained by separating the crystals through filtration. Prior to adding the non-polar solvent, the reaction mixture may be distilled under reduced pressure to distill off a part of the polar solvent from the reaction mixture.

According to this invention, the linear trimer of p-isopropenyl phenol of formula [I] can be easily prepared selectively from p-isopropenyl phenol and/or its linear polymer by performing the reaction for a relatively short period of time. The desired linear trimer can be easily separated as a precipitate from the reaction mixture.

The linear trimer of p-isopropenyl phenol represented by formula [I] obtained as above can be converted, without purification, into useful derivatives by such reactions as epoxidation or hydrogenation. Recrystallization from a suitable organic solvent, for example a lower alcohol such as methanol or ethanol can, of course, afford a linear trimer of higher purity. The high purity linear trimer so obtained can be used as a raw material for thermosetting resins or as a curing agent for epoxy resins either as such or after conversion into its derivatives.

For example, when the unpurified product is hydrogenated in a stream of hydrogen at 200° to 300° C. under atmospheric pressure using 10% Pd on diatomaceous earth as a catalyst, a compound of the following formula is obtained.

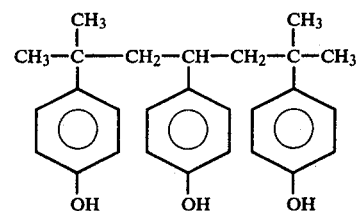

This compound can be used as a curing agent for epoxy resins, and its epoxidation product is useful as a raw material for epoxy resins.

When the linear trimer of p-isopropenyl phenol represented by formula [I] obtained as above is treated, without purification, with epichlorohydrin in the presence of sodium hydroxide, it can be converted to an epoxy compound of the following formula [VI].

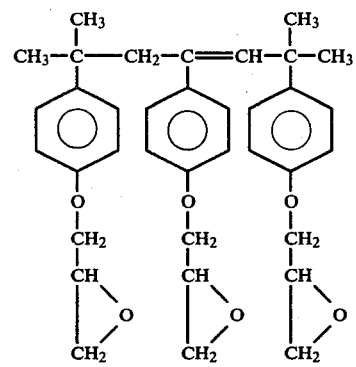

This compound is extremely useful as a raw material for epoxy resins.

In one example of application of the linear trimer of this invention as a curing agent for an epoxy resin, 1 mole of the linear trimer of p-isopropenyl phenol of formula [I] which is purified by recrystallization is mixed with 1.5 moles of a diglycidyl ether of bisphenol A, and after adding a catalytic amount of N,N-dimethylbenzylamine, the mixture is heated at 160° C. for 1 hour to afford a pale yellow clear cured epoxy resin.

The following Examples illustrate the invention more specifically. All parts and percentages in these Examples are by weight.

EXAMPLE 1

A glass reactor was charged with 50 parts of benzene and 100 parts of a mixture of linear polymers of p-isopropenyl phenol which had been prepared by the method disclosed in Japanese Patent Publication No. 10869/77 (consisting of 83% of a dimer, 4.3% of a trimer, 2.1% of a tetramer, 0.9% of a pentamer and 1.5% of a hexamer and higher polymers), and they were maintained at 50° C. Separately, a 10% aqueous solution of hydrochloric acid was prepared, and 0.5 part of the solution was fed into the reactor. With stirring, the reaction was performed at 50° C. for 4 hours. The reaction mixture was then neutralized with a 10% aqueous solution of sodium hydroxide, and the precipitated crystals were separated by filtration. The crystals were dried, and weighed. The weight was found to be 74.5 parts. Recrystallization from methanol afforded 68 parts of a linear trimer of p-isopropenyl phenol of formula [I] having a purity of 98% as determined by gas chromatography and a melting point of 225.5° to 227° C. The resulting linear trimer consisted of more than 95% of the cis-isomer and the remainder being the trans-isomer. The chemical shifts (δ values) of the nuclear magnetic resonance spectrum of the linear trimer in acetone-$D_6$ were as follows;

$$\overset{a}{CH_3}-\overset{a}{\underset{CH_3}{C}}-\overset{c}{CH_2}-\overset{}{\underset{\underset{\phi}{|}}{C}}=\overset{d}{CH}-\overset{b}{\underset{\underset{\phi}{|}}{C}}-\overset{b}{CH_3}$$

(with OH$^f$, OH$^e$, OH$^f$ on the phenyl rings)

| a —$CH_3$ | 0.87 ppm |
|---|---|
| b —$CH_3$ | 1.38 |
| c —$CH_2$— | 2.50 |
| d =CH— | 5.63 |
| e -φ-OH | 7.83 |
| f -φ-OH | 8.00 |

The infrared absorption spectrum (KBr method) of the linear trimer is shown in FIG. 1.

EXAMPLE 2

Example 1 was repeated except that the amount of the benzene was increased to 100 parts, and the amount of the 10% aqueous solution of hydrochloric acid, to 2 parts. There was obtained 83 parts of the same linear trimer of p-isopropenyl phenol as obtained in Example 1.

EXAMPLE 3

Example 1 was repeated except that the reaction was performed at 80° C. There was obtained 40 parts of the same linear trimer of p-isopropenylphenol as obtained in Example 1. Large amounts of a cyclic dimer of p-isopropenyl phenol and bisphenol A were formed as by-products.

EXAMPLE 4

Example 1 was repeated except that 10 parts of methanol was added further as a solvent. After a 4-hour reaction, 50 parts of the same linear trimer of p-isopropenyl phenol as obtained in Example 1 was obtained.

EXAMPLE 5

Example 1 was repeated except that 500 parts of methylene chloride was used as the solvent and the reaction was performed at 25° C. There was obtained 71 parts of the same linear trimer of p-isopropenyl phenol as obtained in Example 1.

EXAMPLE 6

Example 1 was repeated except that 100 parts of a linear dimer of p-isopropenyl phenol having a purity of 98% and containing 85% by weight of 4-methyl-2,4-bis(4-hydroxyphenyl)-pent-1-ene and 15% by weight of 4-methyl-2,4-bis(4-hydroxyphenyl)-pent-2-ene was used as a starting material. There was obtained 88.5 parts of the same linear trimer of p-isopropenyl phenol as obtained in Example 1.

EXAMPLE 7

Example 1 was repeated except that 0.5 part of a 10% aqueous solution of sulfuric acid was used instead of the 10% aqueous solution of hydrochloric acid. There was obtained 53 parts of the same linear trimer of p-isopropenyl phenol as obtained in Example 1.

EXAMPLE 8

A glass reactor was charged with 50 parts of benzene and 100 parts of a linear dimer of p-isopropenyl phenol having a purity of 98% and containing 85% by weight of 4-methyl-2,4-bis(4-hydroxyphenyl)-pent-1-ene and 15% by weight of 4-methyl-2,4-bis(4-hydroxyphenyl)-pent-2-ene, and they were maintained at 50° C. Separately, a 5% carbon tetrachloride solution of a boron trifluoride - ether complex was prepared, and 0.5 part of the solution was fed into the reactor. The reaction was performed at 50° C. for 4 hours. There was obtained 65 parts of the same linear trimer of p-isopropenyl phenol as obtained in Example 1.

EXAMPLE 9

A glass reactor was charged with 100 parts of monomeric p-isopropenyl phenol having a purity of 99.5% and 500 parts of benzene, and with stirring at 10° C., 2.5 parts of p-toluenesulfonic acid was added. After exotherm subsided, the reaction was performed at 35° C. for 3 hours. The crystals that precipitated were separated by filtration, and dried. This product was determined to be the same compound as the linear trimer obtained in Example 1 as a result of its gas chromatographic analysis, infrared absorption spectrum analysis and high-speed liquid chromatographic analysis. The yield of the product was 81.5 parts.

EXAMPLE 10

Example 1 was repeated except that the amount of the 10% aqueous solution of hydrochloric acid was changed to 5 parts, and the reaction was performed at 70° C. for 1 hour. There was obtained 58 parts of a linear trimer of p-isopropenyl phenol of formula [I]. It was confirmed by its gas chromatographic analysis and nuclear magnetic resonance spectrum that this linear trimer is a mixture of 87% of the trans-isomer and 13% of the cis-isomer. Repeated fractional crystallization of this mixture using benzene afforded a substantially pure trans-isomer (m.p. 167°–168° C.). The chemical shifts (δ values) of the nuclear magnetic resonance spectrum of the trans-isomer (in acetone-$D_6$) were as follows:

| —$CH_3$ | 1.04, 1.13 ppm |
|---|---|
| —$CH_2$— | 2.68 |
| =CH— | 5.53 |
| —φ—OH | 8.00 |

The infrared absorption spectrum of this trans-isomer is shown in FIG. 2.

EXAMPLE 11

A glass reactor was charged with 50 parts of a linear dimer of p-isopropenyl phenol (purity 98%) and 30 parts of nitrobenzene, and they were maintained at 60° C. Then, 0.5 part of activated clay was added as an acid catalyst to the reaction system, and with stirring at 60° C., the reaction was performed for 8 hours. The product was not seen to precipitate from the reaction mixture.

A gas chromatographic analysis of the reaction mixture showed the formation of the following compounds (the amounts in % are based on the total amount of the dimer of p-isopropenyl phenol charged).

| Compounds | Amounts (%) |
|---|---|
| Linear trimer (trans-isomer) of formula [I] | 43% |
| Linear trimer (cis-isomer) of formula [I] | 21% |
| Cyclic dimer of p-isopropenyl phenol | 17% |
| Linear dimer (unreacted) of p-isopropenyl phenol | 12% |
| Monomer of p-isopropenyl phenol | 1% |
| Tetramer and higher polymers of p-isopropenyl phenol | 6% |

The reaction mixture was filtered to separate the activated clay. By adding 110 parts of benzene to the filtrate, a white precipitate was formed. The precipitate was separated by filtration, washed, and dried to form 23 parts of a linear trimer of p-isopropenyl phenol of formula [I] consisting of 62% of the trans-isomer and 38% of the cis-isomer.

EXAMPLE 12

A glass reactor was charged with 100 parts of the same mixture of linear polymers of p-isopropenyl phenol as used in Example 1 and 200 parts of dioxane, and they were maintained at 40° C. Then, 1 part of a 10% aqueous solution of sulfuric acid was added, and the reaction was performed at 40° C. for 6 hours. The reaction mixture was a uniform solution and the reaction product was not seen to precipitate.

The reaction mixture was neutralized with an aqueous solution of sodium hydroxide, and then distilled under reduced pressure to distill off 150 parts of the dioxane. To the remaining solution was added 100 parts of benzene to form a white precipitate. The precipitate was collected by filtration, washed, and dried to afford 42 parts of a powdery solid. By a gas-chromatographic analysis, this solid was found to be a linear trimer of p-isopropenyl phenol of formula [I] consisting of 25% of the trans-isomer and 75% of the cis-isomer.

What we claim is:

1. A process for preparing a linear trimer of p-isopropenyl phenol of the formula

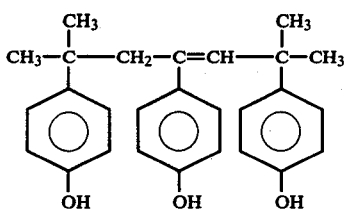

which comprises reacting at least one compound selected from the group consisting of p-isopropenyl phenol and linear polymers of p-isopropenyl phenol in the presence of an acid catalyst in an organic solvent.

2. The process of claim 1 wherein the starting compound is p-isopropenyl phenol.

3. The process of claim 1 wherein the starting compound is a linear polymer of p-isopropenyl phenol represented by the formula

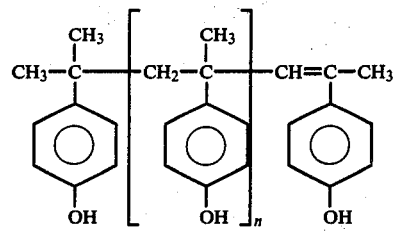

wherein n is 0 or an integer of 1 to 8, or

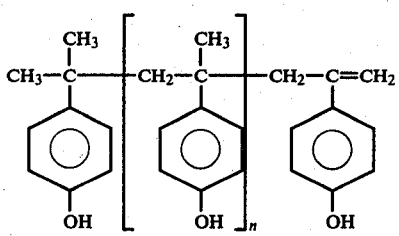

wherein n is 0 or an integer of 1 to 8, or a mixture thereof.

4. The process of claim 1 wherein the starting compound is essentially a mixture of 4-methyl-2,4-bis(4-hydroxyphenyl)-pent-1-ene and 4-methyl-2,4-bis(4-hydroxyphenyl)-pent-2-ene which are linear dimers of p-isopropenyl phenol.

5. The process of claim 1 wherein the starting compound is a mixture of at least 80% by weight of 4-methyl-2,4-bis(4-hydroxyphenyl)-pent-1-ene and 4-methyl-2,4-bis(4-hydroxyphenyl)-pent-2-ene which are linear dimers of p-isopropenyl phenol and not more than 20% by weight of a linear polymer of p-isopropenyl phenol having a degree of polymerization of 3 to 10.

6. The process of claim 1 wherein the organic solvent is an aromatic hydrocarbon, substituted aromatic hydrocarbon or halogenated hydrocarbon.

7. The process of claim 1 wherein the organic solvent is an aprotic polar solvent selected from the group consisting of dioxane, dimethyl formamide, dimethyl acetamide and tetrahydrofuran.

8. The process of claim 1 wherein the organic solvent is a mixture of an aromatic hydrocarbon and not more than 3.0% by weight of water.

9. The process of claim 1 wherein the organic solvent is a mixture of an aromatic hydrocarbon and not more than 70% by weight of an alcohol.

10. The process of claim 1 wherein the acid catalyst is a Lewis acid, protonic acid or solid acid.

* * * * *